United States Patent [19]
Joseph et al.

[11] Patent Number: 5,183,549
[45] Date of Patent: Feb. 2, 1993

[54] MULTI-ANALYTE SENSING ELECTROLYTIC CELL

[75] Inventors: Jose P. Joseph, Menlo Park; Marc J. Madou, Palo Alto, both of Calif.

[73] Assignee: Commtech International Management Corporation, Menlo Park, Calif.

[21] Appl. No.: 470,954

[22] Filed: Jan. 26, 1990

[51] Int. Cl.⁵ ................ G01N 27/404; G01N 27/414
[52] U.S. Cl. .................. 204/415; 204/153.13; 204/153.14; 204/153.17; 204/153.19; 204/153.2; 204/153.21; 204/412; 204/416; 204/418; 204/419; 204/433; 204/435
[58] Field of Search ............ 204/153.17, 415-420, 204/435, 153.13, 153.14, 153.19, 153.2, 153.21, 433, 412

[56] References Cited

U.S. PATENT DOCUMENTS

| | | | |
|---|---|---|---|
| 3,912,614 | 10/1975 | Spracklen et al. | 204/415 |
| 3,997,420 | 12/1976 | Buzza | 204/415 |
| 4,025,412 | 5/1977 | La Conti | 204/432 |
| 4,568,445 | 2/1986 | Cates et al. | 204/415 |

Primary Examiner—T. Tung
Attorney, Agent, or Firm—Fliesler, Dubb, Meyer & Lovejoy

[57] ABSTRACT

An electrolytic sensor is set forth for measuring the amounts of an ionic and of a vaporous species in a liquid. The system has an electrode sensitive to an ionic species and another electrode sensitive to a vaporous species. A unitary membrane covers the electrodes and the requisite electrolyte with the membrane being permeable to the vaporous species, impermeable to the liquid and having dispersed in it an ionophore which senses the ionic species via selective transfer into the membrane of a quantity of the ionic species determined by the concentration of the ionic species in the liquid. Such quantities as hydrogen ion concentration, carbon dioxide concentration and oxygen concentration can be determined by a single electrolytic cell structure.

20 Claims, 1 Drawing Sheet

MULTI-ANALYTE SENSING ELECTROLYTIC CELL

DESCRIPTION

Technical Field

The present invention relates to an electrolytic cell system which is useful for determining the concentrations of an ionic species and of vaporous non-ionic species which are dissolved in a liquid. For example, such a cell system can be used for detecting oxygen, carbon dioxide and hydrogen ion (pH) utilizing a single membrane.

Background of the Invention

Electrolytic cells have been formulated which are capable of analyzing the concentrations of vaporous analytes which are dissolved in a liquid. Such cells have been formulated on substrates by having an electrode on the substrate which is sensitive to the analyte, having an electrolyte in contact with the electrode, having an appropriate reference electrode to complete the circuit, and having a membrane covering the electrode and the electrolyte, which membrane is permeable to the vaporous analyte and impermeable to the liquid. The analyte may be oxygen, carbon dioxide, hydrogen, or virtually any vaporous analyte for which an analysis is desired. The permeability of the membrane can be due to small passages appropriately sized to admit the analyte and/or the analyte can dissolve in the membrane and be transported as a solute through the membrane.

It is also known to analyze for ionic analytes dissolved in a liquid utilizing sensors which include a substrate with an electrode on a sensing surface thereof, an electrolyte contacting the electrode and a membrane covering the analyte and the electrode, the membrane being impervious to the liquid being analyzed but sufficiently pervious to a dissolved ionic analyte to allow, with the use of an appropriate ionophore, the setting up of a potential difference between the liquid and the membrane. For example, such cells find applicability for providing hydrogen ion concentration (pH measurements) and for measuring the concentrations of ionic species such as sodium ion and potassium ion. The ion selective ionophore in the membrane serves to associate with the selected ionic species and draw it partially into the membrane.

If one wants to analyze for both a vaporous species and an ionic species which are both dissolved in the same liquid it is necessary to prepare two separate electrolytic cells each covered by a different and distinct membrane. Thus, the costs of production have been relatively high. Also, it can be very inconvenient to position two different sensors in, for example, a blood vessel.

The present invention is directed to overcoming one or more of the problems as set forth above.

DISCLOSURE OF INVENTION

In accordance with the present invention an electrolytic cell system is set forth for determining the concentrations of an ionic species and of a vaporous species, both of which are dissolved in a liquid. The cell system comprises a substrate having an ionic species sensing area and a vaporous species sensing area. A first electrolyte is in contact with the ionic species sensing area and a second electrolyte is in contact with the vaporous species sensing area. A single membrane covers both sensing areas and both electrolytes. The membrane is permeable to a first vaporous species, impermeable to the liquid, and has dispersed in it an ionophore which senses the ionic species via selective transfer into the membrane of a quantity of the ionio species determined by the concentration of the ionic species in the liquid being analyzed. A first electrode is in contact with the first electrolyte. A second electrode is in contact with the second electrolyte. The electrodes are free from contact with one another.

An electrolytic cell as set forth above has the great advantage that a single membrane acts as an ion sensitive electrode and at the same time as a volatile analyte permeable electrode whereby analysis for both components can be carried out utilizing a substrate encapsulated or covered in a single operation by the single membrane. The only alternative for providing both and ionic species sensitive electrolytic cell and a volatile analyte sensitive cell on the same substrate would be to use two different membranes and to somehow seal them together or to have a portion of the substrate exposed between the two membranes. The added expense in manufacturing would be great even if the technical problems can be solved. In accordance with the present invention a single membrane is set forth which can be contacted with an analyte solution and can provide readouts of several parameters at once, most particularly such parameters as pH, carbon dioxide concentration and oxygen concentration. Such is particularly useful when the entire sensor can be made small and inserted in a blood vessel to provide in situ measurements of such quantities.

BRIEF DESCRIPTION OF DRAWINGS

The invention will be better understood by reference to the figures of the drawings wherein like numbers denote like parts throughout and wherein.

BEST MODE FOR CARRYING OUT INVENTION

Figure 1:
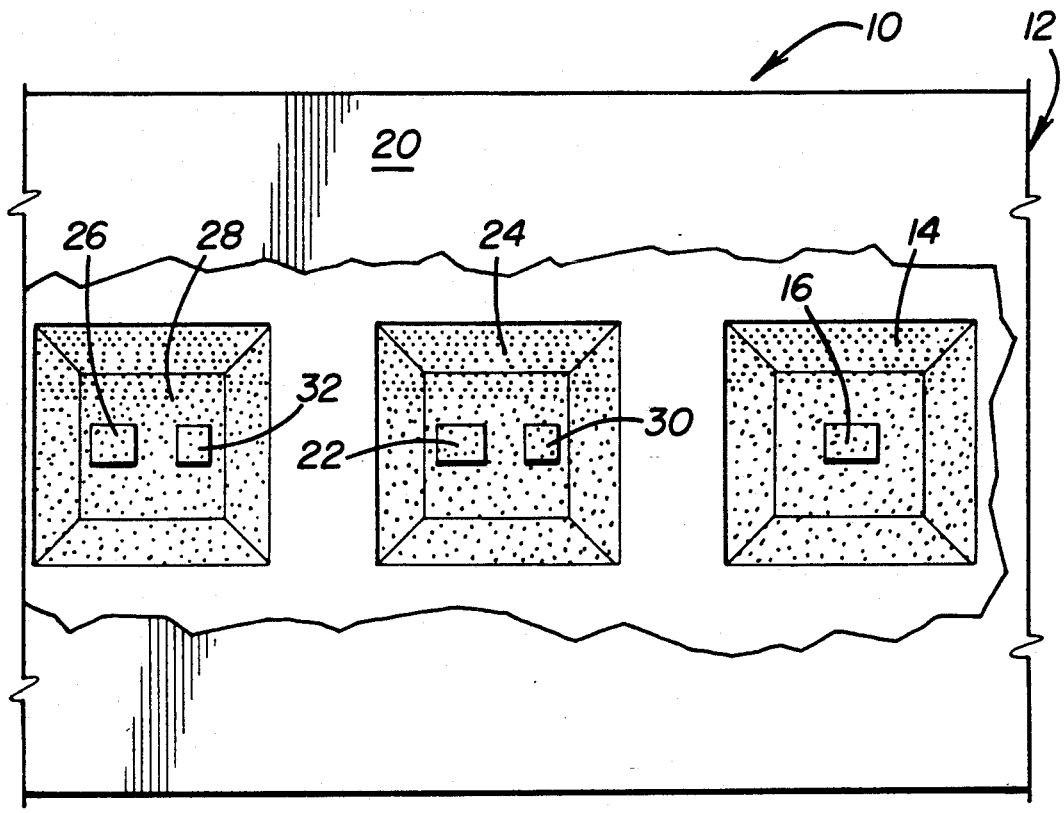
FIG. 1 illustrates, in plan view, partially cut away, an electrolytic cell in accordance with the present invention.
Figure 2:
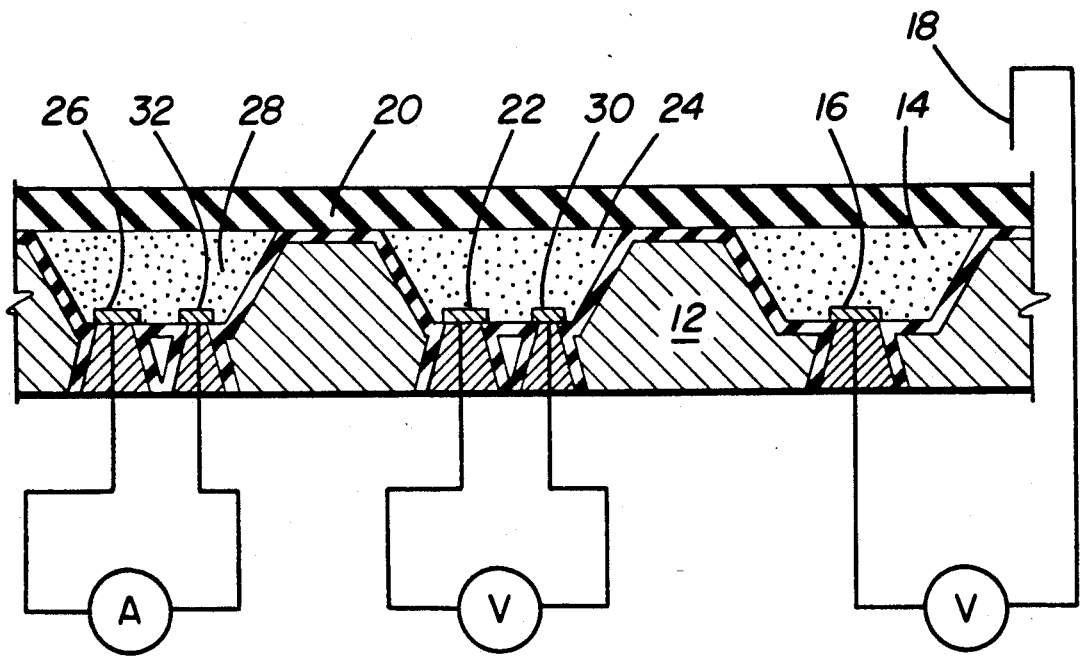
FIG. 2 illustrates the embodiment of FIG. 1 in side elevation, partially in section.

In accordance with the present invention an electrolytic cell structure 10 is set forth for determining the concentrations of both an ionic species and a vaporous species which are dissolved in a liquid, often an aqueous liquid. The electrolytic cell structure 10 is built on a substrate 12 which has a first sensing area 14. A first electrode 16 is on the first sensing area 14. The first electrode 16 is used to determine the concentration of the ionic species. The first electrode 16 is generally a common reference electrode and the potential difference is measured between the liquid being analyzed and an external electrode 18 located in the liquid being analyzed. The first electrode 16 and the external electrode 18 can be of the same type, for example, both can be Ag/AgCl electrodes. The potential difference arises across the surface of the required membrane 20 which is discussed in more detail below.

The substrate 12 may be made of any of a number of materials. For example, the substrate 12 may be made of an insulative material, that is, a dielectric material, such as a non-conducting plastic or glass. Alternatively, the substrate 12 can be made of a semiconducting material such as silicon or even of a conducting material so long as an appropriate dielectric material is present to electrically isolate individual cells which make up the electrolytic cell system 10. For example, the substrate 12 can be silicon having a silicon dioxide dielectric layer on it as formed by IC processing techniques. Silicon nitride or another insulative material can alternatively be used.

A second electrode 22 is also on the substrate 12. The second electrode 22 is capable of sensing a first vaporous species and is in contact with a second electrolyte 24. The first electrode 16 and the second electrode 22 are free from contact with one another. In the embodiment illustrated in FIG. 1 a third electrode 26 is also present on the substrate 12, is in contact with a third electrolyte 28 and is free from contact with the first electrode 16 and the second electrode 22. The third electrode 26 is sensitive to a second vaporous species. In the embodiment illustrated the second electrode 22 can be, for example, a pH sensitive electrode, e.g., $IrO_2$. An internal reference electrode 30, for example, Ag/AgCl, is also in contact with the second electrolyte 24 and the potential difference between the electrodes 22 and 30 would indicate the concentration of the first vaporous species, e.g., $CO_2$, which would pass through the membrane 20. The third electrode 26 can be, for example, an Ag electrode and the internal reference electrode 32 can be Ag/AgCl with a constant voltage being applied between electrodes 26 and 32 and current being measured to determine the concentration of the second vaporous species. If the voltage is $-0.7$ volt and the membrane 20 is selected to be permeable to $O_2$, the concentration of $O_2$ in the liquid can be determined. It should be noted that the above discussion of specific species and electrodes is merely exemplary of the many species that are subject to analysis utilizing the apparatus and/or method of the present invention.

The first electrode 16, and along with it the second electrode 22, and the third electrode 30, when present, can be formulated by vapor deposition, sputtering, or the like. Generally, such techniques as are utilized in the IC art are applicable to formulate an electrolytic cell system 10 in accordance with the present invention.

The substrate 12, as mentioned above, may comprise any of a number of materials and its particular composition is not critical in the invention. However, it is often desirable to have a relatively small substrate 12 so that they can be utilized in situ in such positions as inside of blood vessels. Accordingly, one may make use of the techniques of the semiconductor processing art to make the electrolytic cell system 10 either on or beneath the surface of a semiconductor material, most particularly silicon. Methods for making such cells are set forth in, for example, U.S. Pat. No. 4,765,864 issued Aug. 23, 1988 to C. E. Holland, E. R. Westerberg, M. J. Madou and T. Otagawa.

The term ionic species is used herein to indicate any species which exists as an ion in the liquid being analyzed. The ionic species may be positively charged or negatively charged. For example, the ionic species might be hydrogen, sodium, potassium, or virtually any metal ion. Negative ionic species might include any of the halides, sulfate, nitrate, perohlorate, thiocyanate, acetate, benzoate, salicylate, phenylalaninate, leucinate, or large organic anions, for example, anionic detergents.

The term vaporous species is used to indicate any species which can enter the vapor state from the liquid. For example, such species include hydrogen, oxygen, nitrogen, carbon monoxide, carbon dioxide, nitrous oxide, sulfur dioxide or trioxide, ammonia, hydrogen sulfide, hydrogen cyanide, hydrofluoric acid, acetic acid or halogens.

The liquid in which the ionic and vaporous analytes may be present will often be an aqueous liquid. However, the liquid can be any liquid in which an ionic species and a vaporous species can be dissolved. Thus, the liquid can be methanol, ethanol, n-propanol, isopropanol, glycerol, a glycol, tetrahydrofuran, sorbitol, hydrocarbons or aromatic solvents (for high molecular weight organic anions, for example), ketones or aldehydes.

The electrolyte can include any of the liquids listed above having dissolved therein an appropriate ionic salt such as sodium bicarbonate, ammonium chloride, sodium nitrite, citrate buffer, potassium silver cyanide, sodium acetate, bisulfite buffer, acetate buffer, phosphate buffer, potassium or sodium chloride or generally any non-interfering salt or mixture of salts.

Any of a number of different types of solid electrolytes can be utilized. For example, the solid electrolyte can be a hydrogel. Preferable, however, particularly for voltammetric measurements, are solid electrolytes, including solid polymeric electrolytes such as Nafion (a trademark of DuPont) which is part of a class of solid polymeric ion exchangers which conduct ions upon exposure to water. Probably the best known examples are membranes made from polystyrene with fixed negative sites (sulfonate, carboxylate or phosphonate) or fixed positive sites (quaternary ammonium or quaternary phosphonium). Selection as far as ions are concerned with these materials is almost exclusively on the basis of charge and for ions with the same charge discrimination is very slight. For voltammetric sensing the use of these materials is new. Other examples of solid polymeric electrolytes besides Nafion (which a is perfluorinated ionomer) are sulfonated styrene-divinyl benzene resins and divinyl naphthalene sulfonic acid polymer.

Such polymers are characterized chemically and physically in that they have a hydrophobic nature with ionic (hydrophilic) clusters inside. They conduct ions upon hydration. They exclude co-ions up to the Donnan failure point at which stage ions of both types can penetrate into the resin. Neutral molecules can diffuse readily through such membranes and especially large organic molecules can dissolve within the more hydrophobic resins.

Resins can also be used as reference solutions (see, for example, French patent publication No. 2,158,905). These ion exchange resins have been used as the electrolyte for a potentiometric $CO_2$ sensor (see, for example, U.S. Pat. No. 3,730,868).

Gels useful as electrolytes for incorporation Within the sensor structure include, without limitation: methylcellulose, polyvinyl alcohol, agar, carboxyoellulose, gelatin, agarose, deionized gelatin, polyacrylamide, polyvinyl pyrrolidone, hydroxyethylacrylate, hydroxyethylmethacrylate, and polyacrylic acid. They are characterized in that they constitute thickened (more viscous) solutions. They are hydrophilic in natural and include synthetic polymeric film forming materials.

The electrolyte can alternatively be selected from a family of inorganic oxide solid proton conductors, e.g., hydrogen uranyl phosphate, protonated $\beta''$-alumina, zirconium phosphates or antimonic acids.

The membrane 20 must have certain properties. First of all, it must be insoluble in the liquid. Second, it must be permeable to the vaporous species being analyzed.

Third, it must be impermeable to the liquid. Fourth, it must have dispersed in it an ionophore which allows transfer into the membrane 20 of a portion of the ionic species thus setting up a potential difference at the surface of the membrane 20 which contacts the liquid sample, the magnitude of which potential difference is determined by the concentration of the ionic analyte of interest in the liquid sample.

The membrane 20 may be made of any appropriate polymeric material. Suitable materials include poly(vinylchloride), poly(methylmethacrylate), poly siloxane/poly(bisphenol-A carbonate) block copolymer, poly(bisphenol-A carbonate), polystyrene, polyurethane, silicon rubber or cellulose acetate. Particularly suitable materials are poly siloxane/poly(bisphenol-A carbonate) block copolymer, poly(bisphenol-A carbonate), silicone rubber and polyurethane.

The membrane 20 may be formulated with the necessary permeability to the non-ionic species by including pores in it through, for example, casting it with a volatile solvent included in it and then allowing the solvent to evaporate leaving behind passages of the desired degree of permeability to a species of interest.

Addition of a plasticizer to the membrane also may be necessary. The plasticizer reduces the glass transition temperature of the membrane 20 and at the same time helps to improve the selective permeability of the species of interest. In contrast to the membranes of the prior art which tend to use about two-thirds (2/3rds) as much plasticizer as polymer, the membranes useful in practicing the present invention suitably have less than 60%, more suitably less than 50% and preferably less than 40% as much plasticizer as polymer. Particularly good membranes for the purpose of the invention have been formulated with between 20% and 35% as much plasticizer as polymer.

The ionophores which may be present for allowing transfer of hydrogen are suitably organic amines having usually 15 or more carbon atoms. Monoamines, diamines and triamines each work well. Specific examples of such ionophores are trioctyl amine and tridodeoyl amine.

Ionophores which may be utilized for allowing transfer of various other ionic species are set forth in the following Table I.

TABLE 1

| Ions | Ionophores |
| --- | --- |
| K+ | Valinomycin |
|  | Dicyclohexano-18-crown-6 |
|  | Dibenzo-18-crown-6 |
|  | Tetraphenyl borate |
|  | Tetrakis (p-chlorophenyl) borate |
| Ca++ | bis(didecylphosphate) |
|  | bis(4-octylphenylphosphate |
|  | bis(4-(1,1,3,3-tetramethylbutyl)phenyl phosphate tetracosamethylcyclododecasiloxane |
|  | N,N'-di (11-ethoxycarbonyl) undecyl)-N,N'4,5-tetramethyl-3,6-dioxooctane diamide |
| H+ | Tridodecylamine |
|  | N-methyl N-octadecyl (1-methyl, 2-hydroxy, 2-phenyl)ethylamine |
|  | N-octadecyl 3-hydroxy n-propylamine |
|  | N,N'bis (octadecyl ethylene amine) |
|  | p-octadecyloxy-m-chlorophenylhydrazonemeso oxalonitrile |
| Na+ | Monensin |
|  | N,N',N''-triheptyl-N,N',N''-trimethyl-4,4',4''-propylidintris-(3-oxabutyramide) |
| Li+ | N,N'-diheptyl-N,N',5,5-tetramethyl-3,7-dioxononanediamide) |
|  | 12-crown-4 |

TABLE 1-continued

| Ions | Ionophores |
| --- | --- |
|  | 6,6-dibenzyl-14 crown-4 |
| cl− | Quarternary ammonium chloride |
|  | tri butyl tin chloride |

The ionophore may be incorporated in the membrane 20 by dissolving the ionophore and the membrane material in a common solvent and then casting the membrane 20. Alternatively, the membrane 20 can be first made and then doped with the ionophore later by allowing it to diffuse through the membrane 20.

The various electrodes which are useful in the method and apparatus of the invention can be any of the commonly used reference type electrodes, e. g., silver/silver chloride or calomel electrode. Selectivity to any particular ion arises due to the nature of the ionophore incorporated in the membrane 20. Other types of reference or contact electrodes 16 can also be used. These include, for example, electrodes 16 of platinum, platinum black, silver, gold, iridium, palladium, palladium/silver, iridium dioxide, platinum black/palladium, platinum oxide, and mixtures thereof, electronically conductive polymers, pH sensitive glass electrodes, and generally any of the electrodes normally utilized in electrochemical measurements.

TABLE II

| Stability Of The Potential For Micro ISE vs Glass Electrode | | |
| --- | --- | --- |
| Time in Solution (Hours) | Glass (mV) | ISE (mV) |
| 48 | −57 | 130 |
| 71 | −53 | 135 |
| 99 | −54 | 136 |
| 118 | −59 | 132 |
| 146 | −54 | 139 |
| 218 | −64 | 130 |

Electrodes useful for sensing various vaporous non-ionic species may be made of silver, gold, platinum, palladium, carbon, mercury or other metals. Such electrodes can be modified with different chemicals. Selectivity is provided by the catalytic properties of the electrode and also by the potential applied to the electrodes for effecting reduction or oxidation of the non-ionic species of interest. In determining acidic or basic gases, the electrode can be a pH sensing surface such as a metal oxide, pH sensitive glass or a polymer.

The invention will be better understood by reference to the following illustrative examples.

Cell System Construction

A membrane was formulated and cast in place as follows: 6 mg of potassium tetrakis(4-chlorophenyl) borate, 13.4 mg of tridodecyl amine, 250 mg of bis(2-ethylhexyl) sebacate plasticizer and 1000 mg of polycarbonate-polysiloxane block copolymer were dissolved in 10 ml of tetrahydrofuran.

The membrane was cast upon a silicon substrate having electrodes in wells on the surface. Aqueous gel electrolytes were positioned over the electrodes prior to the casting. The solvent was allowed to evaporate for at least 24 hours. For pH and ion measurements the sensors were conditioned by contact with a solution of the appropriate ion for 10 to 24 hours.

pH Measurement Stability

A pH portion of the cell system used a Ag/AgCl electrode in the cell and in the liquid in which the hydrogen ion concentration was being measured. The response of the sensor was checked against phosphate buffered solutions in the 6.8–7.8 pH range and the sensor was found to give Nernstian responses in this range. The stability of the absolute potential of the sensor was measured at pH 7.4 along with that of a glass pH electrode over a 218 hour period as reported in Table II and was found to be substantially as good as that of the glass pH electrode.

Oxygen Measurement

Oxygen concentration was measured in a cell covered by a membrane as set forth above. The electrodes used were Ag and Ag/AgCl. The electrolyte used was a pHEMA hydrogel. The electrodes were maintained at a constant voltage of $-0.75$ volts. The experiment was carried out at room temperature (about 25° C.) Cathodic current was measured as $O_2$ and Ar were alternately bubbled through a test liquid (water). Approximately a 13 nA increase in cathodic current resulted when $O_2$ was bubbled through the water. This was reproduced through two cycles of $Ar/O_2$.

Industrial Applicability

The present invention provides an electrolytic cell system 10 useful for determining the concentrations of both an ionic species and of one or more vaporous species which are dissolved in a liquid. Very small cells can be formulated which can be inserted in a blood vessel to determine, in situ, such quantities as pH, carbon dioxide concentration and oxygen concentration.

While the invention has been described in connection with specific embodiments thereof, it will be understood that it is capable of further modification, and this application is intended to cover any variations, uses, or adaptations of the invention following, in general, the principles of the invention and including such departures from the present disclosure as some within known or customary practice in the art to which the invention pertains and as may be applied to the essential features hereinbefore set forth, and as fall within the scope of the invention and the limits of the appended claims.

That which is claimed is:

1. A multi-analyte electrolytic sensor for determining the concentrations of an ionic species and of at least one vaporous species, both dissolved in a liquid, comprising:
   a substrate having an ionic species sensing area and a vaporous species sensing area;
   a first electrolyte on said ionic species sensing area;
   a second electrolyte on said vaporous species sensing area;
   a first sensing electrode in contact with the first electrolyte;
   a second electrode in contact with the second electrolyte, said second electrode and said second electrolyte being isolated from said first sensing electrode and first electrolyte; and
   a unitary membrane covering both of said sensing areas and both of said electrolytes, said membrane being permeable to said vaporous species, impermeable to said liquid and having dispersed therein an ionophore which senses said ionic species via selective transfer into said membrane of a quantity of said ionic species determined by the concentration of said ionic species in said liquid.

2. An electrolytic sensor as set forth in claim 1, wherein said substrate further includes an additional vaporous species sensing area; and
   further including:
   a third electrolyte in contact with said additional vaporous species sensing area; and
   a third electrode in contact with said third electrolyte, said third electrode and said third electrolyte being isolated from said first and second electrodes and said first and second electrolytes and said third electrode being sensitive to a second vaporous species.

3. An electrolytic sensor as set forth in claim 2, wherein said first vaporous species is oxygen and said second vaporous species is carbon dioxide.

4. An electrolytic sensor as set forth in claim 3, wherein said ionic species is hydrogen ion.

5. An electrolytic sensor as set forth in claim 1, wherein said ionic species is hydrogen ion.

6. An electrolytic sensor as set forth in claim 1, wherein said membrane comprises silicon rubber.

7. An electrolytic sensor as set forth in claim 1, wherein said ionic species is hydrogen, a metal ion, a halide, sulfate, nitrate, perohlorate, thiooyanate, acetate, benzoate, salicylate, phenylalaninate, leuoinate, or a large organic anions having at least 15 carbon atoms.

8. An electrolytic sensor as set forth in claim 7, wherein said vaporous species is hydrogen, oxygen, nitrogen, carbon monoxide, carbon dioxide, nitrous oxide, sulfur dioxide, sulfur trioxide, ammonia, hydrogen sulfide, hydrogen cyanide, hydrofluoric acid, acetic acid or a halogen.

9. An electrolytic sensor as set forth in claim 8, wherein said first electrolyte and said second electrolyte are each independently selected from the group consisting of methanol, ethanol, n-propanol, isopropanol, glycerol, a glycol, tetrahydrofuran, sorbitol, a hydrocarbon solvent, an aromatic solvent, a ketone and an aldehyde having dissolved therein an ionic salt.

10. An electrolytic sensor as set forth in claim 9, wherein said salt is sodium bicarbonate, ammonium chloride, sodium nitrite, citrate buffer, potassium silver cyanide, sodium acetate, bisulfite buffer, acetate buffer, phosphate buffer, potassium chloride or sodium chloride.

11. An electrolytic sensor as set forth in claim 10, wherein said membrane is a poly(vinylchloride) polymer, a poly(methylmethacrylate) polymer, a poly siloxane/poly(bisphenol-A carbonate) block copolymer, a poly(bisphenol-A carbonate) polymer, a polystyrene polymer, a polyurethane polymer, a silicon rubber polymer or a cellulose acetate polymer.

12. An electrolytic sensor as set forth in claim 11, wherein said electrolytes are solid polymer electrolytes or hydrogels.

13. An electrolytic sensor as set forth in claim 1, wherein said vaporous species is hydrogen, oxygen, nitrogen, carbon monoxide, carbon dioxide, nitrous oxide, sulfur dioxide, sulfur trioxide, ammonia, hydrogen sulfide, hydrogen cyanide, hydrofluoric acid, acetic acid or a halogen.

14. An electrolytic sensor as set forth in claim 13, wherein said first electrolyte and said second electrolyte are each independently selected from the group consisting of methanol, ethanol, n-propanol, isopropanol, glyoerol, a glycol, tetrahydrofuran, sorbitol, a hydrocarbon solvent, an aromatic solvent, a ketone or an aldehyde having dissolved therein an ionic salt.

15. An electrolytic sensor as set forth in claim 14, wherein said salt is sodium bicarbonate, ammonium chloride, sodium nitrite, citrate buffer, potassium silver cyanide, sodium acetate, bisulfite buffer, acetate buffer, phosphate buffer, potassium chloride or sodium chloride.

16. An electrolytic sensor as set forth in claim 15, wherein said membrane is a poly(vinylchloride) polymer, a poly(methylmethacrylate) polymer, a poly siloxane/poly(bisphenol-A carbonate) block copolymer, a poly(bisphenol-A carbonate) polymer, a polystyrene polymer, a polyurethane polymer, a silicon rubber polymer or a cellulose acetate polymer.

17. An electrolytic sensor as set forth in claim 1, wherein said first electrolyte and said second electrolyte are each independently selected from the group consisting of methanol, ethanol, n-propanol, isopropanol, glycerol, a glycol, tetrahydrofuran, sorbitol, a hydrocarbon solvent, an aromatio solvent, a ketone or an aldehyde having dissolved therein an ionic salt.

18. An electrolytic sensor as set forth in claim 17, wherein said salt is sodium bicarbonate, ammonium chloride, sodium nitrite, citrate buffer, potassium silver cyanide, sodium acetate, bisulfite buffer, acetate buffer, phosphate buffer, potassium chloride or sodium chloride.

19. An electrolytic sensor as set forth in claim 18, wherein said membrane is a poly(vinylohloride) polymer, a poly(methylmethacrylate) polymer, a poly siloxane/poly(bisphenol-A carbonate) block copolymer, a poly(bisphenol-A carbonate) polymer, a polystyrene polymer, a polyurethane polymer, a silicon rubber polymer or a cellulose acetate polymer.

20. An electrolytic sensor as set forth in claim 1, wherein said membrane is a poly(vinylchloride) polymer, a poly(methylmethacrylate) polymer, a poly siloxane/poly(bisphenol-A carbonate) block copolymer, a poly(bisphenol-A carbonate) polymer, a polystyrene polymer, a polyurethane polymer, a silicon rubber polymer or a cellulose acetate polymer.

* * * * *